(12) United States Patent
Esnouf

(10) Patent No.: US 7,383,736 B2
(45) Date of Patent: Jun. 10, 2008

(54) DEVICE AND METHOD FOR PRESSURE INDICATION

(75) Inventor: Philip Stuart Esnouf, Richmond (AU)

(73) Assignee: Ultimate Medical Pty Ltd, Richmond (AU)

( * ) Notice: Subject to any disclaimer, the term of this patent is extended or adjusted under 35 U.S.C. 154(b) by 66 days.

(21) Appl. No.: 10/515,950

(22) PCT Filed: May 23, 2003

(86) PCT No.: PCT/AU03/00634

§ 371 (c)(1),
(2), (4) Date: Sep. 2, 2005

(87) PCT Pub. No.: WO03/099365

PCT Pub. Date: Dec. 4, 2003

(65) Prior Publication Data

US 2006/0150742 A1  Jul. 13, 2006

(30) Foreign Application Priority Data

May 24, 2002  (AU) ..................................... PS2559

(51) Int. Cl.
*G01L 13/02* (2006.01)
*G01L 7/06* (2006.01)
*A62B 9/02* (2006.01)
*A61M 29/00* (2006.01)

(52) U.S. Cl. .................. 73/716; 73/729.1; 604/100.01; 604/97.03; 128/205.23

(58) Field of Classification Search ............ 128/205.23; 604/100.1, 97.03; 73/146.8, 716
See application file for complete search history.

(56) References Cited

U.S. PATENT DOCUMENTS

| 3,911,904 | A | | 10/1975 | Saba ...................... 128/2.05 G |
| 3,993,064 | A | * | 11/1976 | McCarthy et al. .......... 604/294 |
| 4,114,458 | A | * | 9/1978 | Alinari ...................... 73/729.1 |
| 4,310,104 | A | * | 1/1982 | Takatsuki ................... 222/131 |
| 4,501,273 | A | * | 2/1985 | McGinnis ............... 128/207.15 |
| 4,966,035 | A | | 10/1990 | Huang ....................... 73/146.8 |
| 5,103,670 | A | | 4/1992 | Wu et al. ................... 73/146.8 |
| 5,336,183 | A | | 8/1994 | Greelis et al. ................ 607/97 |
| 5,439,178 | A | * | 8/1995 | Peterson ..................... 239/333 |
| 5,722,955 | A | * | 3/1998 | Racz .......................... 604/121 |
| 5,878,295 | A | * | 3/1999 | Katagiri et al. ............. 396/348 |
| 5,935,084 | A | * | 8/1999 | Southworth ................. 600/561 |
| 6,042,092 | A | * | 3/2000 | Shibata ....................... 267/122 |
| 6,485,471 | B1 | * | 11/2002 | Zivitz et al. ................ 604/212 |
| 7,018,359 | B2 | * | 3/2006 | Igarashi et al. ......... 604/100.01 |

FOREIGN PATENT DOCUMENTS

| EP | 0 962 231 | | 12/1999 |
| GB | 2 250 596 | | 6/1992 |
| GB | 2 348 607 | | 10/2000 |
| JP | 2001061965 A | * | 3/2001 |

* cited by examiner

*Primary Examiner*—Edward Lefkowitz
*Assistant Examiner*—Jonathan Dunlap
(74) *Attorney, Agent, or Firm*—Seed IP Law Group PLLC

(57) ABSTRACT

A device for indicating an internal pressure of an inflatable medical cuff, comprising: a membrane movable in response to a difference between the internal pressure and an external pressure; and movable indication means operably associated with the membrane for indicating, in use of the device, the internal pressure.

20 Claims, 12 Drawing Sheets

DEVICE AND METHOD FOR PRESSURE INDICATION

FIELD OF THE INVENTION

The present invention relates to a method and device for pressure indication. In particular, the invention relates to a method and device for indicating an air pressure of a cuff of a laryngeal mask or other airway device.

BACKGROUND OF THE INVENTION

In 1988, Dr. Archie Brain invented a new airway device, called the laryngeal mask, for delivering anaesthetic gases and oxygen to an unconscious patient during an operation. Prior to this, patients were commonly anaesthetised using an Endotrachael Tube running through the vocal cords of the patient into the trachea. Alternatively, a face mask connected to a gas source was held over the patient's nose and mouth.

In use, the laryngeal mask is inserted into the pharangeal space (throat) deflated, and when correct positioning is observed, an inflatable cuff around the outside of the mask is inflated with air using a syringe. The syringe is inserted into an end of a valve which is connected to the cuff by a small tube, such that air passed through the valve from the syringe is used to inflate the cuff. There are presently eight different sizes of the laryngeal mask available, and while all require different volumes of air to inflate the cuff, the maximum recommended intra cuff pressure is 60 cm $H_2O$.

The Laryngeal Mask is now the preferred choice of anaesthetists in many countries, and its use continues to grow. The greater prevalence in use of the laryngeal mask has brought certain possible dangers to light. Due to human errors and the possible diffusion of nitrous oxide into the silicone cuff, the cuff may be excessively inflated. Such excessive inflation of the cuff has the potential to damage nerves and tissues around the hypopharynx, and this potential danger has been the subject of scientific papers in anaesthesia journals.

In order to prevent over-inflation of the cuff, it is desirable to check the intra cuff pressure when the laryngeal mask is in place. Currently, the means for checking the air pressure of the cuff include a small inflatable bulb in fluid communication with the cuff inflation tube. To get an indication of the cuff pressure, medical personnel squeeze the bulb under slight pressure from their figures to thus subjectively judge the intra cuff pressure. Alternatively, a manometer may be connected to the cuff inflation valve in order to obtain an accurate pressure measurement. Manometers are, however, relatively expensive and somewhat bulky and can be inconvenient to connect to the cuff inflation valve as the valve is usually close to the patient's mouth.

Similar problems can occur in other airway devices having an inflatable cuff, such as endotracheal tubes, for example.

The present invention attempts to address or ameliorate one or more of the shortcomings of the prior art, or to at least provide a useful alternative thereto.

SUMMARY OF THE INVENTION

The present invention provides, in one aspect, a device for indicating an internal pressure of an inflatable medical cuff, comprising:
a membrane movable in response to a difference between said internal pressure and an external pressure; and
movable indication means operably associated with said membrane for indicating, in use of the device, said internal pressure.

Preferably, the internal fluid volume of the membrane is at atmospheric pressure, while the external fluid volume is at the internal cuff pressure. Preferably, the membrane is closed at one end and open to atmospheric pressure at the other end.

Preferably, the membrane and movable indicator are housed in a hollow body of the device. Preferably, the hollow body is at least partly transparent. Preferably, the hollow body is autoclavable and formed of one of polysulphone, Lexan (polyphalate carbonate) and Ultem (polyetherlmide). Alternatively, the device may be non-autoclavable and disposable, in which case polyvinylchloride (PVC) can be used for some or all of the device materials. Preferably, the hollow body is cylindrical and has scale markings thereon with which a position of the movable indicator may be compared to indicate the internal cuff pressure.

The pressure indication device has distal and proximal ends, the proximal end being defined as the end of the device which is connectable to a cuff inflation tube, while the distal end is defined as being opposite to the proximal end. In one embodiment, the proximal end has a male luer for providing a removable fluid connection to the cuff inflation tube. In another embodiment, the proximal end is directly and non-removably connected to the cuff inflation tube.

Preferably, the distal end of the device is adapted to connect to a syringe. In one embodiment, the distal end includes a spring loaded valve and a female luer and is arranged so that the valve is actuated upon insertion of the syringe into the female luer, thereby opening the valve and allowing fluid communication from or into the syringe into or from the device. In an alternative embodiment, a stopper valve is used instead of the spring loaded valve. The stopper valve operates to provide a similar effect.

Preferably, the membrane is a bellows. Preferably, the bellows is formed of silicone. Preferably, a wall thickness of the bellows is about 0.3 to 0.5 millimeters. More preferably, the thickness is about 0.4 millimeters. Preferably, pleats of the bellows have an opening angle of about sixty degrees when the bellows is in a relaxed state. Preferably, a flange is provided at the open end of the bellows for engaging a rebate in the proximal end of the device. Preferably, inner and outer chambers are defined by the membrane and the hollow body, where the inner chamber is the internal fluid volume of the membrane and the outer chamber is the external fluid volume bounded by the hollow body on the outside and the membrane on the inside. Preferably, the outer chamber includes a substantially annular chamber between a wall of the hollow body and the membrane and an end chamber between the distal end of the device and the closed end of the membrane, the end chamber and annular chamber being separated by the movable indicator.

Preferably, the movable indicator is connected to the membrane at the closed end thereof. Preferably, the movable indicator is formed as a disk having a peripheral flange. Preferably, the flange has one or more channels therein for allowing fluid communication between the end and the annular chambers. Alternatively, the channels may be provided in an inner part of the disk instead of the flange. Preferably, the flange has an indication mark on an outside surface thereof, the mark being visible through said hollow member. Advantageously, the indication mark co-operates with markings on the hollow body to provide an indication of whether the cuff pressure is at a safe pressure.

A further aspect of the invention provides a bellows for use in a pressure indication device for inflatable medical cuff, the bellows having:

an open end and a closed end;

indication means disposed proximate said closed end for providing a pressure indication;

said closed end being movable relative to said open end in response to differential pressure between regions outside and inside of the bellows, such that said indication means is movable to indicate said differential pressure.

Preferably, the inside region is at atmospheric pressure, while the outside region is at an internal cuff pressure of a cuff of a laryngeal mask. Preferably, the open end has a vent to atmospheric pressure. Preferably, the open end has a flange connectable to a bellows holding member. Preferably, the indication means includes a movable indicator connected to said closed end by connection means. Preferably, the connection means includes a boss formed on said closed end. Preferably, the bellows is formed of silicone, has a wall thickness of about 0.4 millimeters and has pleats having an opening angle of about sixty degrees in a relaxed state of the bellows.

In a further aspect of the invention there is provided a pressure responsive device, including:

a hollow body;

a membrane disposed within said hollow body and defining inner and outer chambers within said hollow body, the membrane being responsive to differential pressure between said inner and outer chambers; and a movable indicator disposed toward a closed end of the membrane, the movable indicator being visible through said hollow body for indicating said differential pressure.

A still further aspect of the invention provides a method of determining an internal pressure of a cuff of a laryngeal mask or other airway device, including providing a pressure indication device at a cuff inflation tube of the laryngeal mask or other airway device, the pressure indication device having a membrane moveable in response to a difference between side internal pressure and an external pressure and a movable indicator operably associated with said membrane for indicating said internal pressure, and viewing said movable indicator to determine said internal pressure.

Preferably, if the determined internal pressure of the cuff is below a minimum level indicated on the pressure indication device, the method further includes connecting a syringe to the pressure indication device and injecting air into the cuff inflation tube from the syringe through the pressure indication device. Alternatively, if the determined internal pressure of the cuff is above a maximum level indicated on the pressure indication device, the method further includes connecting a syringe to an end of the pressure indication device and withdrawing air from the cuff inflation tube through the pressure indication device into the syringe. Preferably, following or during withdrawal or injection of air from or into the cuff inflation tube, the method further includes performing the viewing step again.

In another aspect, the invention provides a laryngeal mask having a pressure indication device as described above connected thereto. In another aspect, the invention provides a laryngeal mask having a pressure responsive device as described above connected thereto.

In another aspect, the invention provides a method of administering a breathing gas to a patient, including locating a cuff of a laryngeal mask adjacent a hypopharynx of a patient, the laryngeal mask having a pressure indication device as described above connected to a cuff inflation tube of the laryngeal mask, inflating the cuff, determining an internal pressure of the cuff according to the method described above, adjusting the internal pressure of the cuff according to the determined cuff pressure, and administering the breathing gas to the patient through the laryngeal mask.

The pressure indication device may advantageously be used with other medical devices having an air-inflatable cuff, including for example, endotracheal tubes, laryngeal tubes, naso-tracheal tubes, univent tubes and combitudes. The pressure indication device is also applicable to airway management devices (AMDs) and Portex laryngeal masks.

Advantageously, the pressure indication device of the invention is small and easily connected to, or integrally formed on the end of, the cuff inflation tube of the airway device so as to provide a simple and easily referenced indication of the internal cuff pressure. This means that medical personnel can easily obtain an objective measure of the cuff pressure without having to connect a manometer to the cuff inflation tube. The pressure indication device and methods of use therefor may advantageously reduce the incidence of damage to the hypopharynx area of a patient due to over-inflation of the cuff of the laryngeal mask or damage otherwise resulting from inadequate inflation or over-inflation of an inflatable medical cuff.

Embodiments of the invention are hereinafter described, by way of example only with reference to the accompanying drawings.

DETAILED DESCRIPTION OF THE EMBODIMENTS

Embodiments of the invention are described hereinafter generally in relation to their applicability to laryngeal masks. It should be understood, however, that the invention is also applicable to other applications requiring pressure, indications of a similar magnitude and to other airway devices having air-inflatable cuffs, such as some endotrachial tubes.

Figure 1:
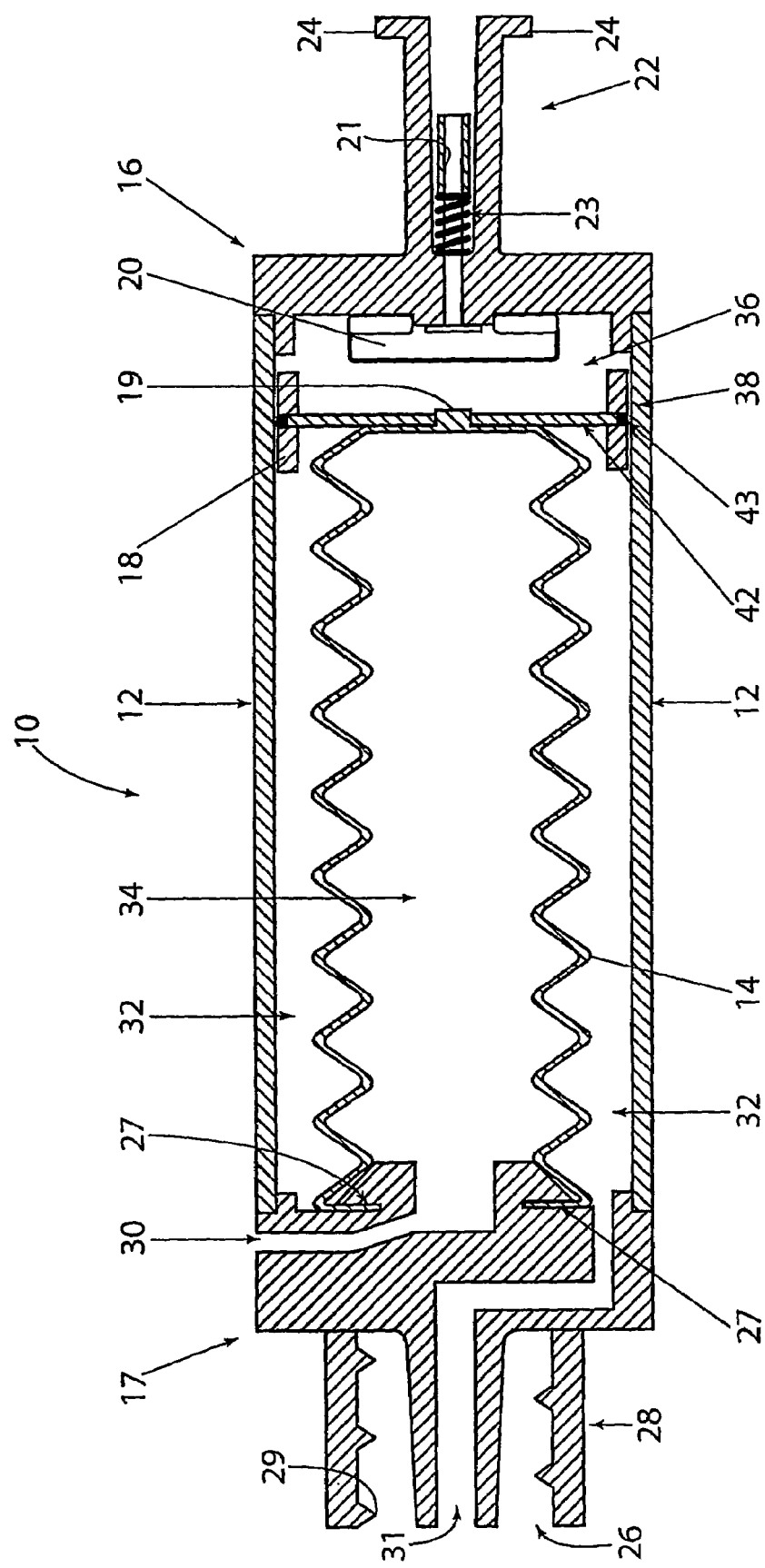
FIG. 1 is a side cross-sectional view of a pressure indication device of an embodiment of the invention.

Referring to FIG. 1, one embodiment of the invention relates to a pressure indicator device 10 having a cylindrical outer wall 12, a bellows 14 and female and male ends 16, 17 (also referred to as the distal and proximal ends, respectively). The bellows 14 is located inside the outer wall 12 and moves concentrically therewithin in response to differential pressure. One end of the bellows 14 is attached to the male end 17, while the other end of the bellows, in its relaxed state, extends towards the female end 16. At the male end 17, the bellows is open to atmospheric pressure via a vent passage 30, while the other end of the bellows 14 is closed and has a boss 19 disposed thereon. The boss 19 engages a hole 39 in an indicator 38 connected to the bellows 14 at the closed end thereof.

The outer wall 12 is formed of polysulphone or alternatively another substantially clear autoclavable material such as Lexan (polyphalate carbonate) and Ultem (polyetherlmide). The outer diameter of the outer wall 12 is preferably between about 9 millimeters and 15 millimeters and ideally about 12.8 millimeters (which is about 0.5 inches). The clarity of the outer wall 12 allows the position of the indicator 38 to be seen through the outer wall 12. The length of the device 10 is preferably in the order of about 40 mm total, although this may vary somewhat, depending on requirements.

The location of the bellows 14 within the outer wall 12 and the female and male ends 16, 17 serve to define an inner chamber 34 within the bellows 14, which is at atmospheric pressure due to the vent passage 30, and an outer chamber 32 defined by the roughly annular space between the bellows 14 and the outer wall 12 and between the closed end of the bellows 14 and the female end 16. This outer chamber 32 is in fluid communication with the cuff inflation line through a male luer outlet passage 31 so that, in use of the indicator device 10, the outer chamber 32 is at the same pressure as the cuff of the laryngeal mask and the inner chamber 34 is at atmospheric pressure. This differential pressure causes the bellows 14 to contract from its elongated relaxed state, thereby moving the indicator 38. The bellows 14 is calibrated so as to consistently contract or compress to the same degree in response to the same cuff pressure.

Figure 2:
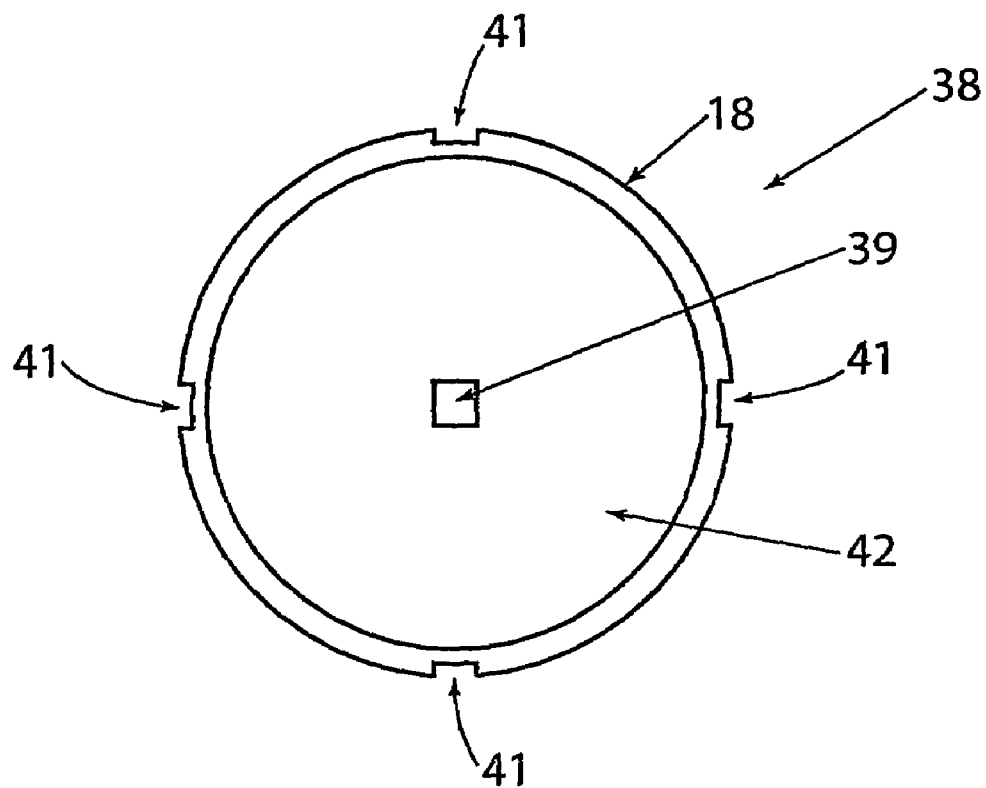
FIG. 2 is an end view of an indicator plate for use in the indication device shown in FIG. 1.

The indicator 38 has a runner 18 which has a substantially parallel surface to that of the interior surface of the outer wall 12 so as to keep an indication mark 43 (which runs circumferentially around the outside of the runner 18) substantially perpendicular to the direction of travel of the bellows along an axial center of the indicator device 10 and to keep the movement of the bellows 14 substantially axially centered. As shown in FIG. 2, the indicator 38 is formed of a circular disk 42 with the runner 18 constituting a peripheral annular flange extending perpendicularly to the plane of the plate in both directions. The plate 42 has the hole 39 in the center thereof for receiving boss 19 in order to attach the indicator 38 to the bellows 14. A suitable adhesive may be used as well as, or instead of, the mechanical connection of the boss 19 and hole 39. The runner 18 has a number of channels 41 in its outer surface extending in the axial direction of the indication device 10 for allowing fluid communication from an end chamber 36 adjacent to the female end 16 with the annular part of outer chamber 32 bounded by the outer wall 12 on the outside and the pleats of the bellows 14 on the inside. As an alternative to the channels 41 being formed on the outside of the runner 18, they may be formed in the plate 42 towards an outer circumference thereof, but not so central as to be blocked by the end of the bellows 14 adjacent to the boss 19.

The runner 18 effectively provides a means of stabilizing the axial movement of the bellows under compression or relaxation. Other stabilizing means may be provided, however, such as a pin attached at the closed end of the bellows 14 in place of boss 19 and extending axially within a fixed guiding sheath anchored toward or at the female end.

The male end 17 of the indication device 10 is formed so as to provide the vent passage 30 to the inside of the bellows 14 and an outlet passage 31 for connection to the cuff inflation line. The male end 17 is formed as a male luer fitting 26, having the outlet passage 31 at the center thereof, an outer male luer wall 28 and a female luer thread 29 on the inside of the luer wall 28 for engaging a male thread of a female luer fitting, if necessary. The male end 17 also has a circular rebate 27 for receiving an end flange 56 (shown in FIG. 5) of the bellows 14. The end flange 56 is secured in the rebate 27 by a suitable adhesive for providing an air tight seal under pressures in the order of 60 cm $H_2O$.

The male end 17 is, in the embodiment pictured in FIG. 1, formed separately to the outer wall 12. However, an alternative embodiment of the invention provides that the male end 17 be formed integrally with the outer wall 12, in which case the axial orientation of the bellows 14 is reversed and the vent passage 30 and rebates 27 are provided in an altered female end 16. Similarly, the embodiment shown in FIG. 1 illustrates that the female end 16 is formed separately to the outer wall 12, but in an alternative embodiment, these are formed integrally, without the need for joining the two portions with adhesives. In a preferred embodiment, the male end 17 is formed separately to the outer wall 12 but has the bellows 14 attached thereto during assembly, while the outer wall 12 and female end 16 are formed integrally and are placed over the bellows 14 and adhered to the male end 17 by suitable adhesives such an alternative embodiment is shown, for example in FIG. 8. Regardless of whether the outer wall 12 is formed integrally with the male and/or female end 17, 16, the axial orientation of the bellows 14 may be reversed (e.g. so that the open end of the bellows 14 is connected to the female end 16 on a rebate suitably formed therein and the closed end extends towards the male end 17).

The female end 16 has a spring-loaded stop valve 20 housed therein which is normally closed to seal off the outer chamber 32 (including end chamber 36) at the female end 16. The valve 20 can be opened in response to depression of a valve actuator 21 against the action of a spring 23. Once the actuator 21 is released, the spring 23 acts against the actuator 21 to return it to its normal extended position and hence close the valve 20. The actuator 21 extends within a female luer fitting 22 whereby, when a male luer fitting is inserted into the female luer fitting 22, the actuator 21 is depressed, thus opening the valve 20. This would occur if, for example, a male luer fitting on the end of a syringe were inserted into the female luer fitting 22. With the actuator 21 depressed, the valve 20 is opened and air from the syringe can be injected into the outer chamber 32. The female luer fitting 22 is provided with female luer bosses 24 for engagement with a male luer thread, such as that shown on syringe 70 in FIG. 4 by reference numeral 74.

Figure 3:
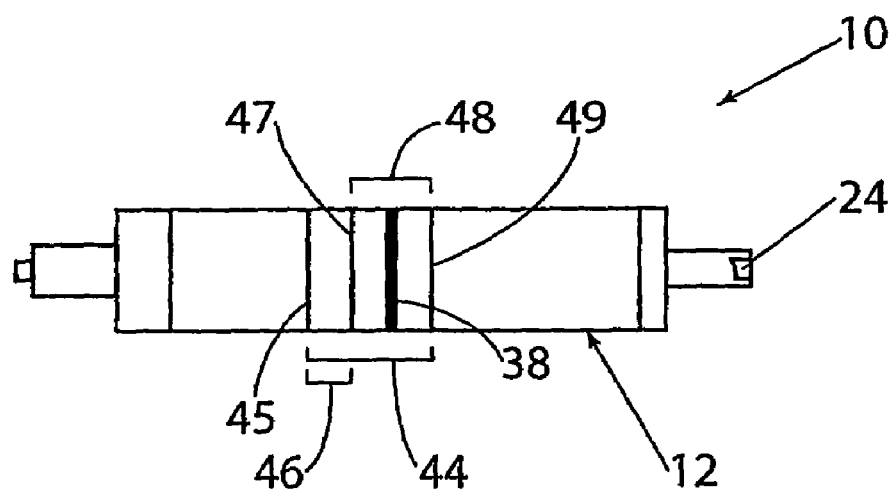
FIG. 3 is a side view of the indication device of FIG. 1, showing example markings on the outside of the device.

Referring now to FIG. 3, the pressure indication device 10 has an indication region 44 around the circumference of the outer wall 12 for providing a scale against which to compare the position of the indicator 38. The indication region 44 includes an over-pressure band 46 and an at-pressure band 48. The over-pressure band 46 has an upper indication bound 45 defining the upper bound of the indication region 44 and over-pressure band 46. A maximum pressure line 47 separates the over-pressure band 46 from the at-pressure band 48, the maximum pressure line 47 corresponding to an intra cuff pressure of 60 cm $H_2O$. The at-pressure band 48 has a lower indication bound 49, below which the corresponding intra cuff pressure is considered sub-optimal. The at-pressure band 48 represents a range of pressures below the maximum pressure of 60 cm $H_2O$ which are considered to be within an optimal intra cuff pressure range, such that when the indicator 38 is visible in the at-pressure band 48, the cuff pressure does not need to be altered. If the indicator 38 is visible above the maximum pressure line 47, air should be withdrawn from the cuff until the indicator 38 enters the at-pressure band 48. If the indicator 38 is visible beyond the upper indication bound 45, this indicates extreme over-pressure of the cuff, and the cuff pressure should be reduced immediately. In a preferred embodiment, the over-pressure band 46 is lightly colored in red, while the at-pressure band 48 is lightly colored in green, with the indicator mark 43 of the indicator 38 being visible through the outer wall 12 as a black line circumferentially running around the outside of the runner 18. The coloring of the over-pressure band 46 and at-pressure band 48 should not be so dark as to obscure the visibility of the indicator mark 43. The at-pressure band 48 may, for example represent pressures between 55 and 60 cm $H_2O$, while the over-pressure band 46 may represent pressures between, say, 60 and 64 cm $H_2O$. Other pressure ranges may be appropriate for airway devices other than the laryngeal mask.

Figure 4:
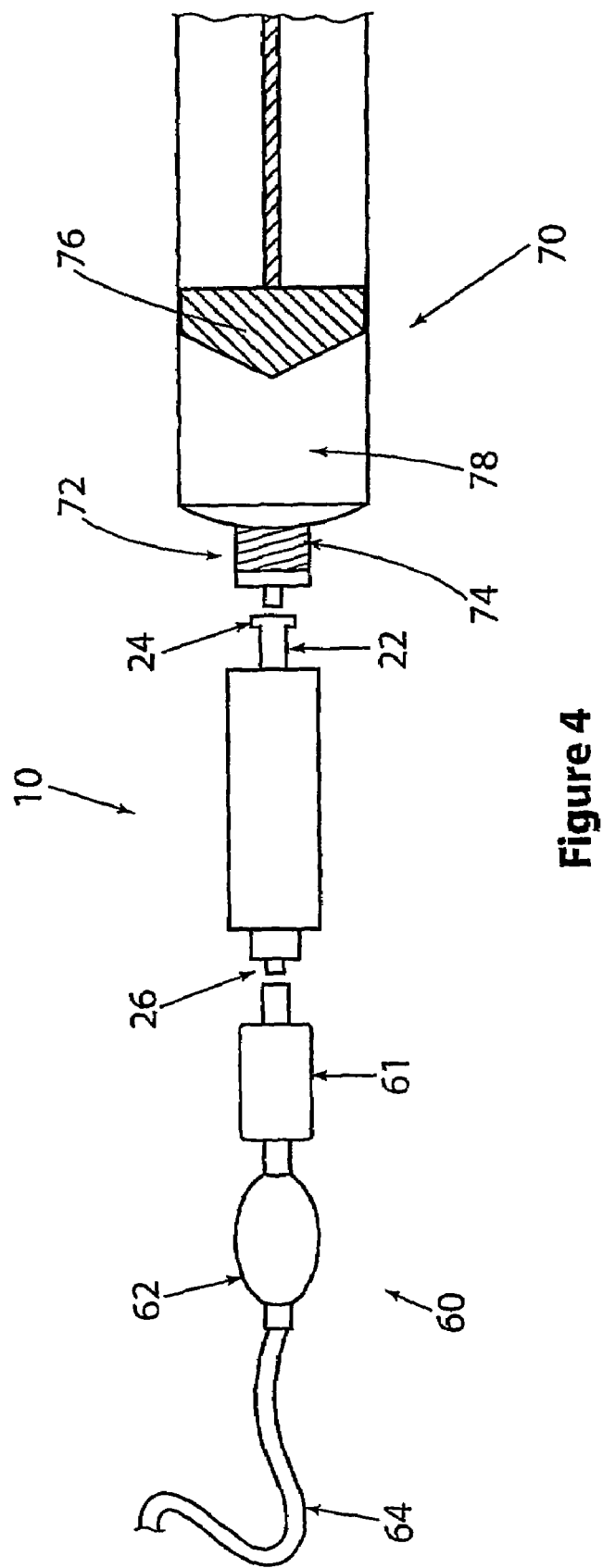
FIG. 4 illustrates an example of use of a pressure indication device of an embodiment of the invention with a cuff inflation line and a syringe.

Referring now to FIG. 4, an illustration of use of the pressure indication device 10 is described. The male luer fitting 26 is insertable into the standard female luer fitting of a cuff inflation line 60. The cuff inflation line 60 has an inflation valve 61 housing the female luer fitting, a cuff pressure indicator balloon 62 connected to the inflation valve 61 on the cuff side thereof and a cuff inflation tube 64 connecting the cuff (not shown) with the cuff pressure indicator balloon 62.

When the pressure indication device 10 is fitted onto the cuff inflation line 60 by inserting the male luer fitting 26 into the female luer fitting of the inflation valve 61, the inflation valve 61 is actuated (opened). This then provides fluid communication from the cuff inflation tube 64 through to the outer chamber 32 of the pressure indication device 10, whereupon, if the cuff pressure is greater than atmospheric, the bellows 14 will be compressed due to the pressure difference, resulting in visible movement of the indicator 38 within or relative to the indication region 44. Relevant medical personnel can then read the relative pressure within the cuff from the position of the indicator 38 within or relative to the indication region 44.

If the position of the indicator 38 relative to the indication region 44 indicates that the cuff pressure is too great or too small, the medical personnel can then withdraw or inject air from or into the cuff by using a syringe 70. This is done by inserting a male luer 72 of the syringe 70 into the female luer fitting 22 of the pressure indication device 10 and twisting the syringe 70 so as to engage the male luer thread 74 with the female luer bosses 24. The insertion of the syringe male luer 72 into the female luer fitting 22 actuates the valve 20 and thereby allows air to be withdrawn or injected from or into the outer chamber 32 (via end chamber 36) and thence from or into the cuff inflation line 60. The injection or withdrawal of air is performed by movement of a plunger 76 within the syringe 70. This plunger 76 seals an end chamber 78 in the end of the syringe 70 so as to maintain the pressure in the cuff inflation line 60 during the cuff pressure adjustment.

While adjusting the air pressure in the cuff, the medical personnel monitor the position of the indicator 38 relative to the indication region 44 so as to ensure optimal cuff pressure is obtained (i.e. by locating the indicator 38 within the at-pressure band 48). Thus, the pressure indication device 10 advantageously allows an initial check of the internal cuff pressure, subsequent adjustment of the cuff pressure using a syringe and continuous cuff pressure monitoring during and after use of the syringe 70. This is a better and more objective means of determining the cuff pressure than by manually finger-squeezing the cuff pressure indicator balloon or by periodically or sequentially taking pressure measurements with a manometer, which involves detaching the manometer and attaching a syringe each time the cuff pressure needs to be adjusted.

Figure 5:
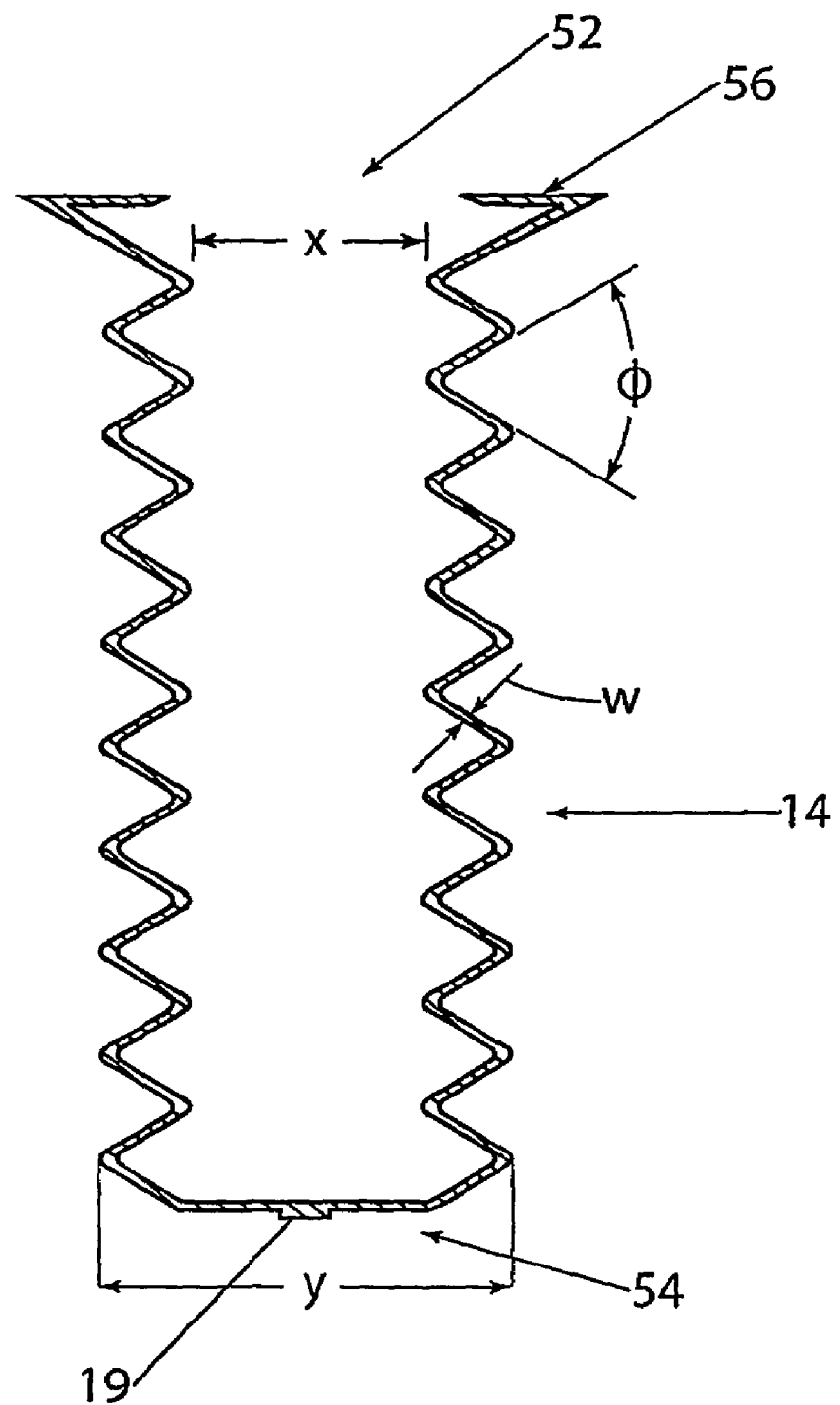
FIG. 5 is a side cross-sectional view of a bellows according to an embodiment of the invention.

Shown in FIG. 5 is an embodiment of the bellows 14 in a relaxed state. The bellows 14 is formed of silicone and has a wall thickness, w, of about 0.3 to 0.52 millimeters, but preferably closer to 0.3 mm. The thickness of the bellows is greater however, at a closed end 54 where the boss 19 is located and may be slightly increased at the flange 56 at its open end 52. In its relaxed state, the length of the bellows 14 is about 28 millimeters and pleats of the bellows 14 open at an angle, $\phi$, of about sixty degrees. The inner diameter, x, of the bellows 14 is preferred to be about 5 millimeters, and is more preferably about 4.9 millimeters. An outer diameter, y, of the bellows 14 is preferred to be about 9.6 millimeters, and more preferably 9.62 millimeters. The precise dimensions, thickness, length, opening angle, number of pleats and configuration of the bellows may be subject to some variation while still being capable of performing the invention. The silicone bellows 14 is preferably formed of silicone rubber having shore hardness A 40 to 60. Depending on the shore hardness of the bellows 14, the location of the indication region 44 on the outer wall 12 will vary in proximity to the proximal and distal ends of the indication device 10. The precise location of the indication region 44 and maximum pressure line 47 is determined by calibration using a manometer.

Figure 6:
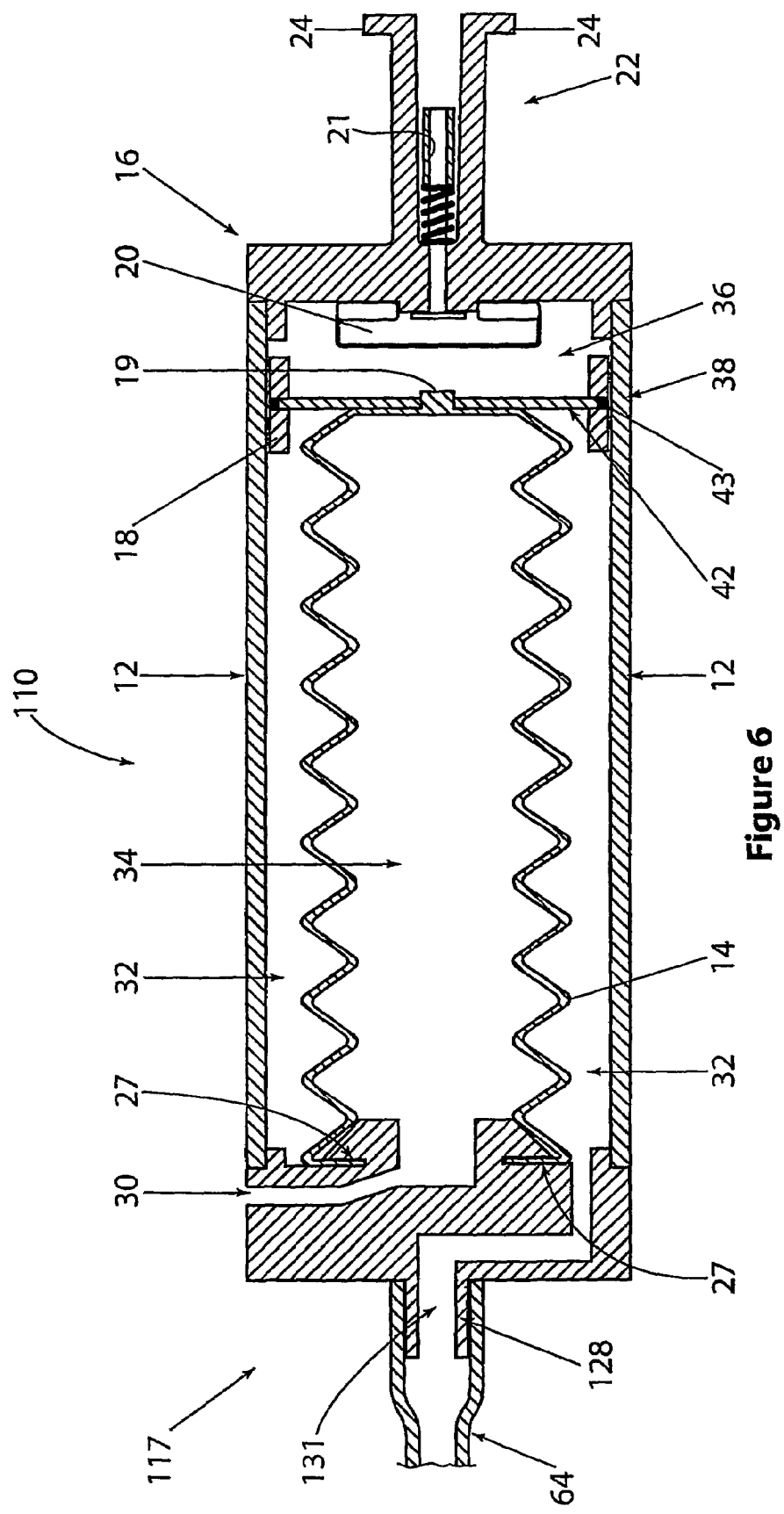
FIG. 6 is a side cross-sectional view of a pressure indication device of another embodiment of the invention.

FIG. 6 illustrates an alternative embodiment of the pressure indication device, represented by reference numeral 110. The pressure indication device 110 is substantially the same as the embodiment shown in FIG. 1 and designated by reference numeral 10, except that it is intended for permanent connection to the cuff inflation tube 64 in place of the inflation valve 61 and cuff pressure indicator balloon 62.

Like reference numerals in FIG. 6 represent like features and the preceding description of those features applies to this embodiment.

In pressure indication device 110, a male end 117 is provided without a male luer fitting but instead having an outlet 128 to which the cuff inflation tube 64 is connected (for example, by suitable adhesives), and the outer chamber 32 is then placed in fluid communication with the cuff inflation tube 64 through outlet passage 131. Instead of having a protruding tubular outlet 128 such as that illustrated in FIG. 6, the cuff inflation tube 64 may otherwise be fixed to the male end 117 so as to be in fluid communication with the outer chamber 32.

Advantageously, the pressure indication device 110 is assembled as part of a laryngeal mask assembly 125 (see FIG. 7) so as to replace the cuff pressure indicator balloon and inflation valve 62, 61 and obviate the need to connect and disconnect the pressure indication device 10 to the cuff inflation line 60 of the laryngeal mask. The pressure indication device 110 is intended to be fitted to a reusable laryngeal mask or other airway device and must therefore be autoclavable. Advantageously, the materials selected for the device 110 (and 10) are all autoclavable.

Figure 7:
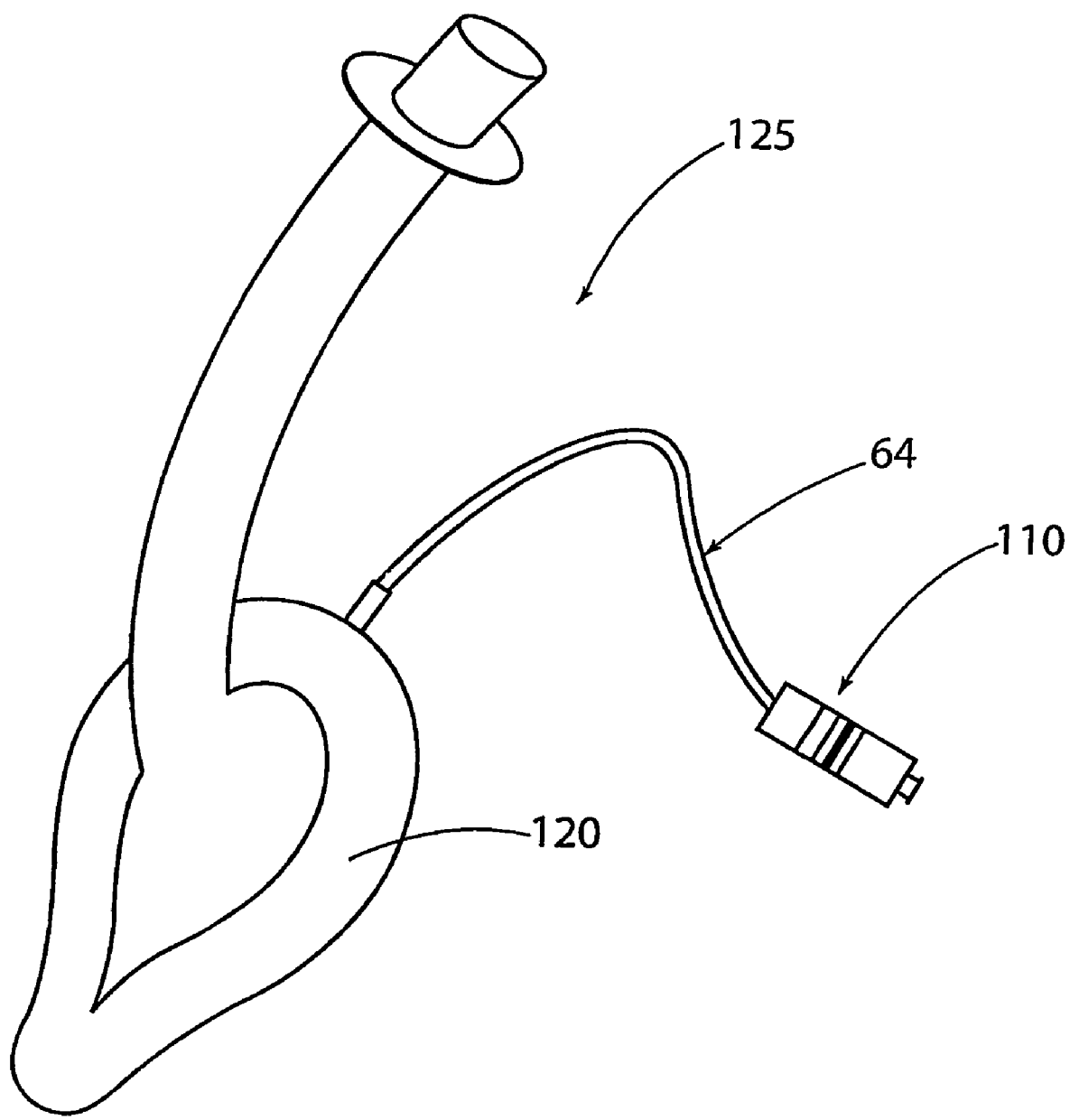
FIG. 7 is an illustration of a laryngeal mask having the pressure indication device shown in FIG. 6.

An example of a laryngeal mask having the pressure indication device 110 assembled as part thereof is shown in FIG. 7, designated by reference numeral 125. FIG. 7 shows the pressure indication device 110 connected at the end of cuff inflation tube 64, which is in-turn connected to the cuff 120.

Referring now to FIGS. 8 to 14, a further embodiment of the pressure indication device is shown, designated by reference numeral 210. This embodiment is similar to the previously described embodiments in many respects, including, for example, its functional interaction with the cuff inflation tube and syringe and in having markings on its cylindrical body for facilitating the pressure indication function. This embodiment is different, however, in that a different embodiment of the bellows is employed, together with modified female and male ends. For purposes of clarity and ease of understanding, the following description of this further embodiment will focus on functional differences between this embodiment and the previously described embodiments. Where different features are not mentioned, this implies that the relevant functional features are the same or similar between the embodiments.

Figure 8:
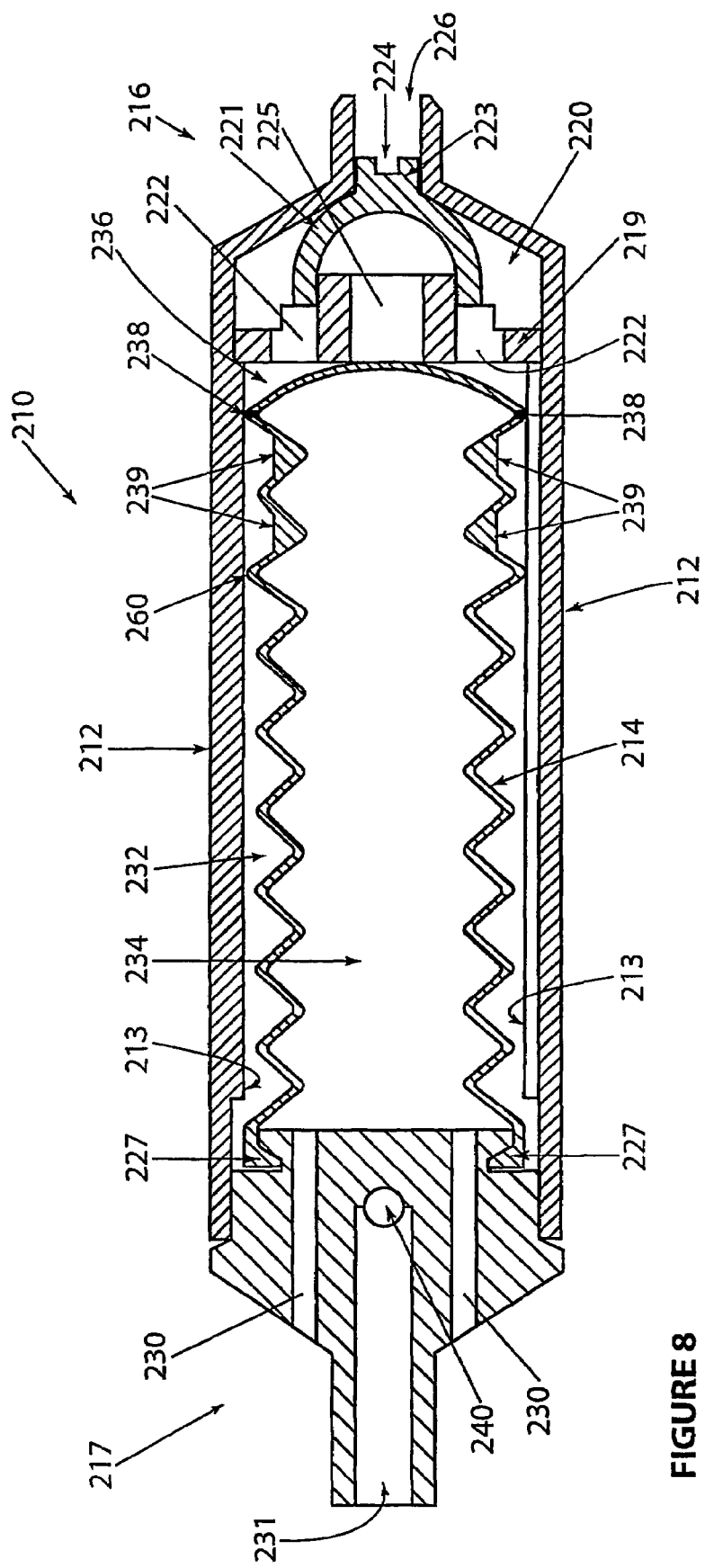
FIG. 8 is a side cross-sectional view of a pressure indication device according to a further embodiment of the invention.

Referring to FIG. 8 specifically, pressure indicator device 210 has an outer wall 212 for housing a bellows 214 and has a male end 217 and oppositely disposed female end 216. The bellows 214 is affixed by a suitable adhesive to a rebate portion 227 of the male end 217 and the male end 217 is fixed similarly to the outer wall 212. Materials used in this embodiment are generally the same as those used in the embodiments previously described and thus the adhesives chosen to affix the bellows 214 to the male end 217 and the male end 217 in turn to the outer wall 212 should therefore be suitable for adhering (for example) silicone to Lexan and Lexan to Lexan, respectively. In this embodiment, the outer wall of female end 216 is integrally formed with outer wall 212. From outer wall 212, female end 216 tapers frustoconically toward an end opening 226. Apart from being fixed to the male end 217, the bellows 214 is moveable longitudinally within the body of the device 210 in response to a pressure difference between inner chamber 234 and outer chamber 232. The inner chamber 234 is bounded by the inside walls of the bellows 214 and the male end 217 but is vented to atmosphere through atmospheric vent passages 230 in the male end 217.

The outer chamber 232 is bounded by the outer wall 212 and the outer surface of the bellows 214. The outer wall 212 has a number of internal wall ribs 213 (better illustrated in FIGS. 10A and 10B) which protrude from the internal wall surface of outer wall 212 by about 0.25 mm. These internal wall ribs 213 serve to act as a guiding means for stabilizing the bellows 214 as it moves within the outer wall 212. Between the internal wall ribs 213 there is an interrupted annular gap through which fluid may communicate past the largest diameter pleats (described further below) of the bellows 214.

An outlet passage 231 in the male end 217 has an outlet fluid communication channel 240 (shown in FIGS. 11A, 11D and 11E) which communicates with the outer chamber 232 so as to place the outer chamber 232 at the internal cuff pressure when the male end of the device 210 is fitted to the cuff inflation tube. At the other end of the device 210, the outer chamber 232 includes a female end chamber 236 which communicates through the female end 216 to a syringe when valve 220 is actuated.

Valve 220 includes a valve support plate 219 seated against the end of the internal wall ribs 213 and supporting a valve stopper 221. The valve stopper 221 is generally hemispherical and hollowed and somewhat cup-shaped, with a concave face facing toward the bellows 214. The stopper 221 has a head portion 223 disposed on its outer convex face for fitting into and loosely engaging the female end opening 226. In its relaxed state, the stopper 221 sits against the inside wall of the female end 216 adjacent the female end opening 226. This interior wall portion contacted by the stopper is generally frustoconical such that, when the outer convex surface of the stopper 221 sits against that portion of the interior wall of the female end 216, female end opening 226 is occluded. Even in its relaxed state, the stopper 221 is still slightly compressed between the frustoconical interior wall of female end 216 and the valve support 219 so as to seal the valve 220. The stopper 221 rests, at its bottom or outer annular edge, against a stopper support flange 228 (shown in FIGS. 12A, 12B and 12C).

Figure 12C:
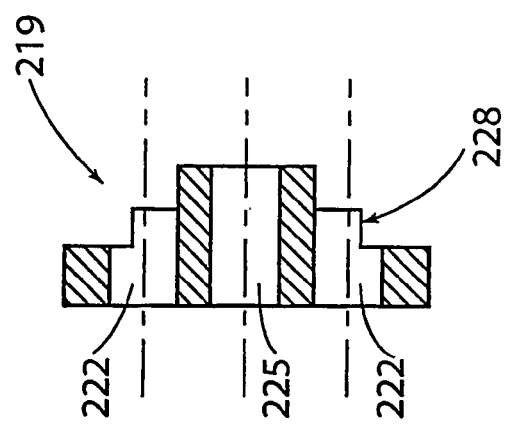
FIG. 12C is a side cross-sectional view of the valve plate shown in FIG. 12B, taken along the lines A-A.
Figure 12B:
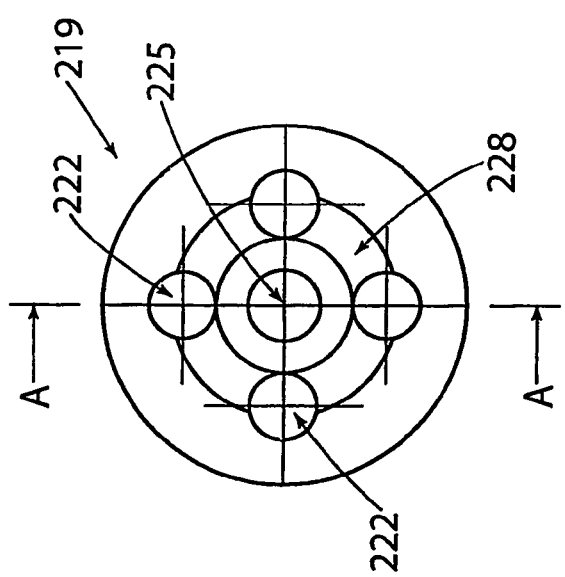
FIG. 12B is an end view of the valve plate shown in FIG. 12A.
Figure 12A:
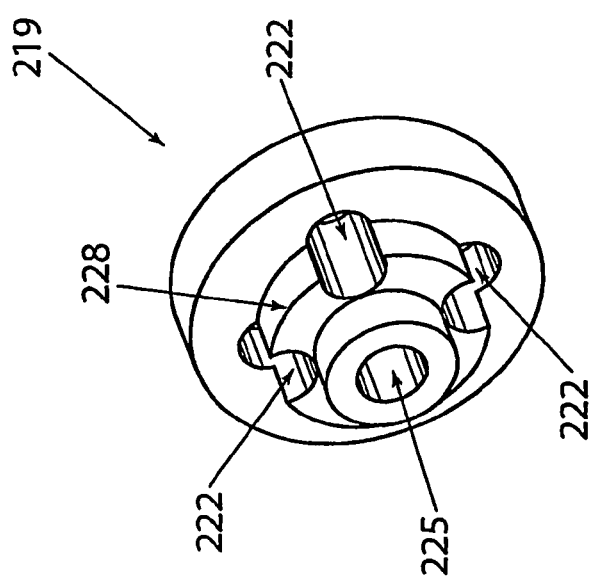
FIG. 12A is an isometric view of a valve plate used in the pressure indication device shown in FIG. 8.
Figure 14:
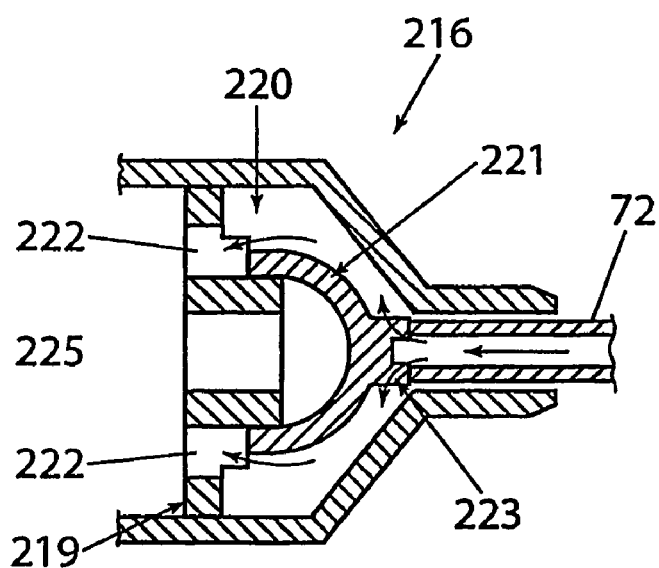
FIG. 14 is a partial cross-sectional side view of a female end of the pressure indication device of FIG. 8, illustrating the stopper in a compressed state whereby fluid communication is enabled.

The stopper 221 has a channel or notch 224 formed in its head portion 223. This channel 224 allows passage of fluid from the syringe around the head portion 223 and into the female end 216 when the stopper 221 is depressed by the syringe nozzle (in its compressed state), as shown in FIG. 14. With reference also to FIG. 14, when the stopper 221 is depressed by the insertion of the syringe nozzle 72 into the female end opening 226, the outer convex surface of the stopper 221 adjacent head portion 223 is moved away from the interior frustoconical wall of female end 216, leaving a gap therebetween. Also, as head portion 223 does not itself occlude the female end opening 226, but rather leaves a small gap, this allows fluid to flow from the syringe nozzle 72 through the head channel 224, around the head portion 223 and through the gap created between the outer convex wall of the stopper 221 and the interior frustoconical wall of the female end 216. The fluid is then free to flow through female end fluid channels 222 in the valve support plate 219. The female end fluid channels 222 are formed as a number, for example 4, of holes formed toward a radially outer peripheral area of the valve support plate 219 (as shown in FIGS. 12A, 12B and 12C). The direction of fluid flow into female end 216 from syringe head 72 is depicted in FIG. 14 by small arrows. Fluid may flow similarly in the other direction in response to suction from the syringe when the stopper is compressed.

The valve support plate 219 has a center hole 225 in the center thereof in communication with the concave underside of stopper 221. Center hole 225 serves to prevent a vacuum forming inside the stopper 221 after it is compressed. Such a vacuum would hinder the stopper 221 from returning its relaxed state and would thus impair the function of valve 220. As can be appreciated from the described arrangement, the natural state of valve 220 is closed, due to the tendency of the flexible stopper 221 to return to its relaxed state, by which it occludes female end opening 226. To accomplish this, the stopper 221 is preferably formed of silicone rubber and has a minimum shore hardness A60.

Figure 9:
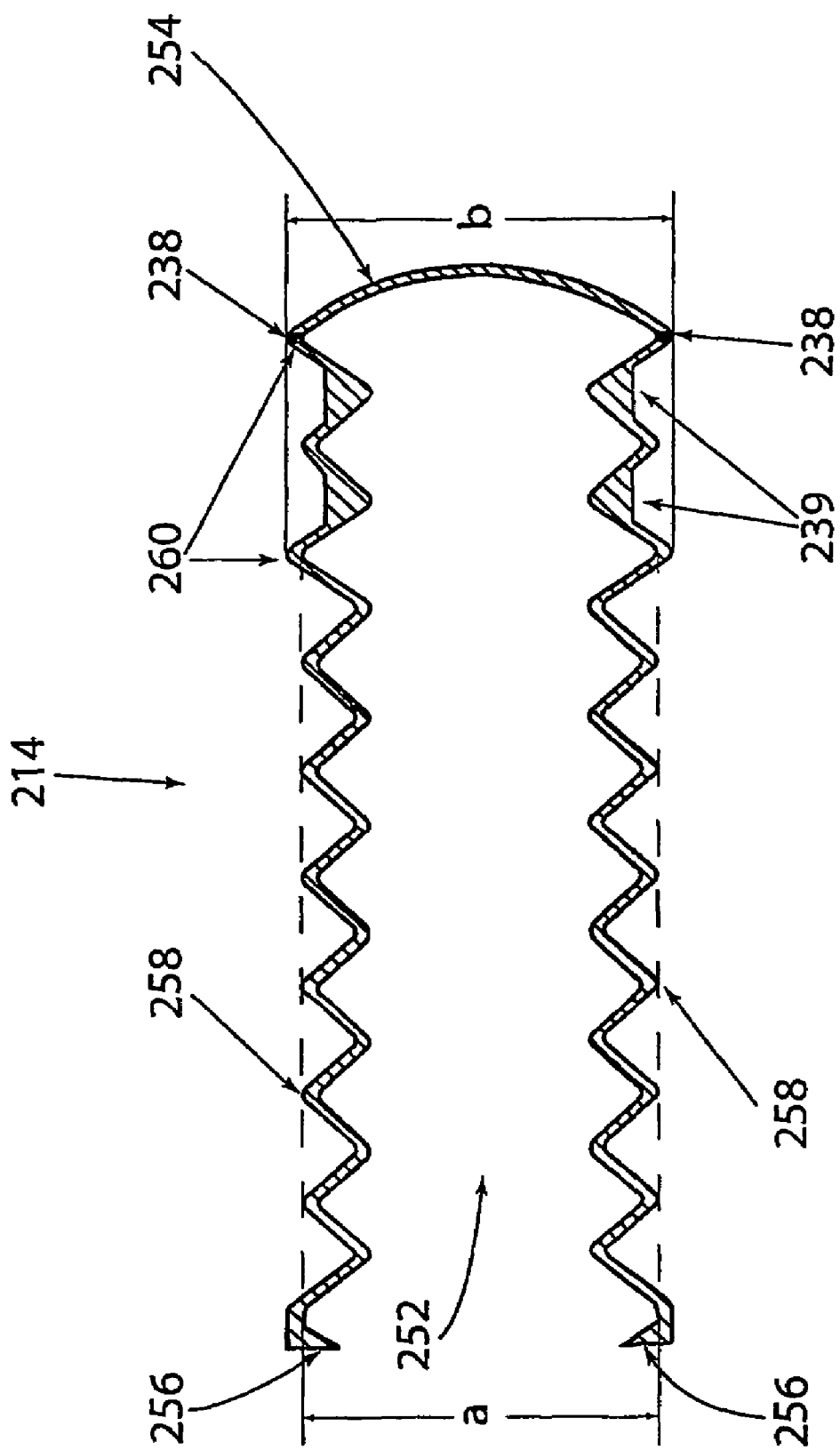
FIG. 9 is a side cross-sectional view of a bellows according to a further embodiment of the invention.
Figure 10A:
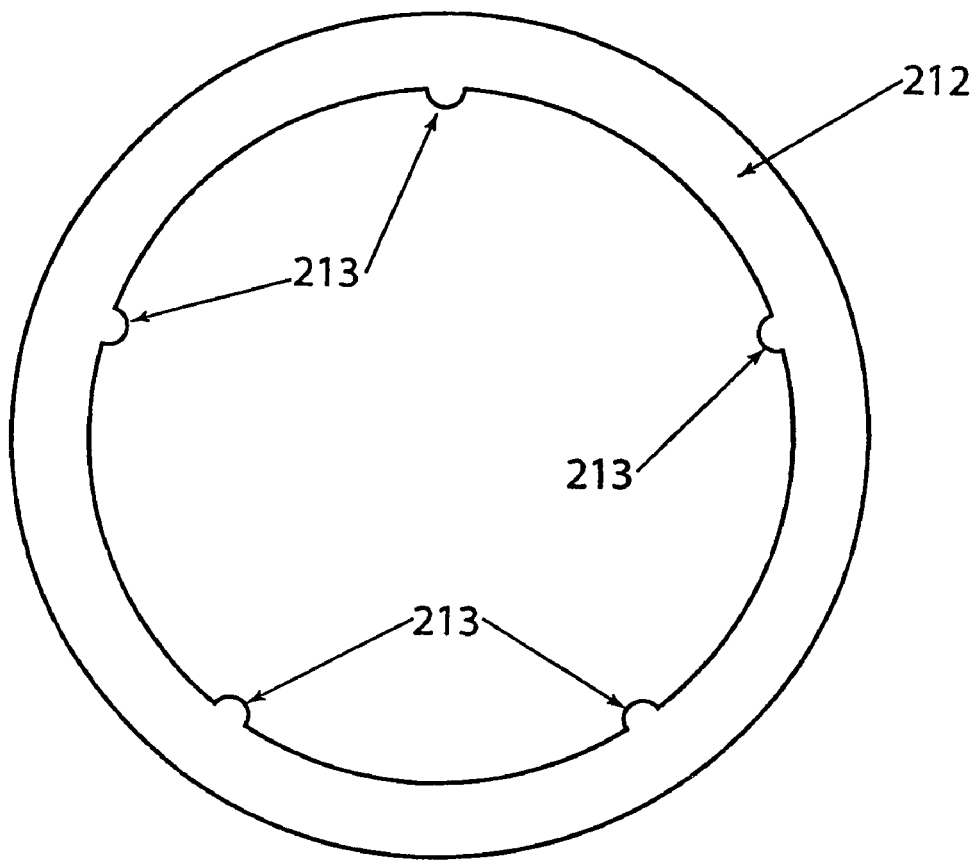
FIG. 10A is an end side cross-sectional view of a hollow tube for use in the pressure indication device.
Figure 10B:
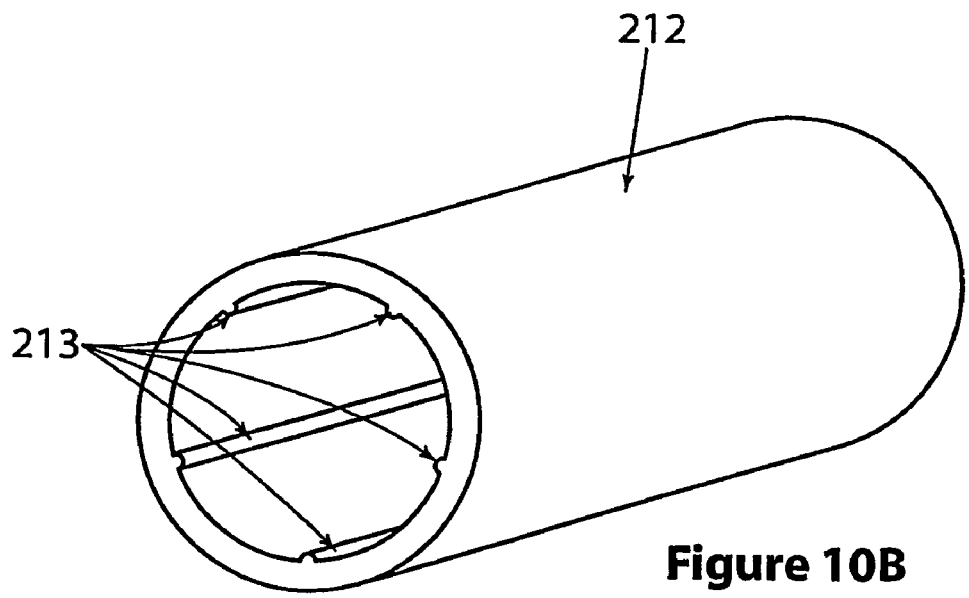
FIG. 10B is an isometric view of the hollow body of FIG. 10A.
Figure 11A:
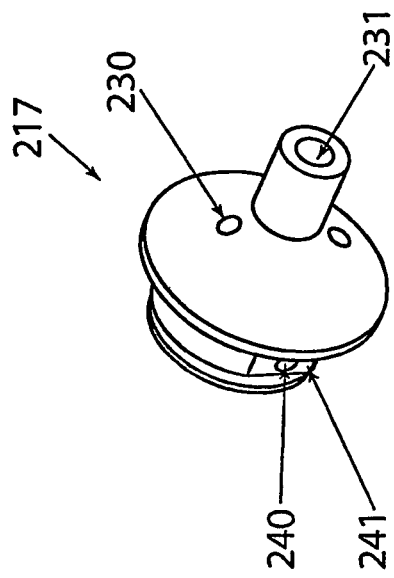
FIG. 11A is an isometric view of a male end of the pressure indication device shown in FIG. 8.
Figure 11C:
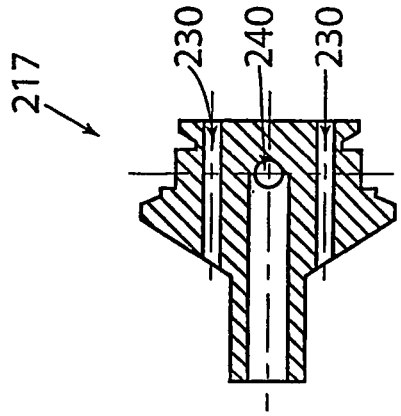
FIG. 11C is a cross-section view taken along lines B-B of the male end shown in FIG. 11B.
Figure 11B:
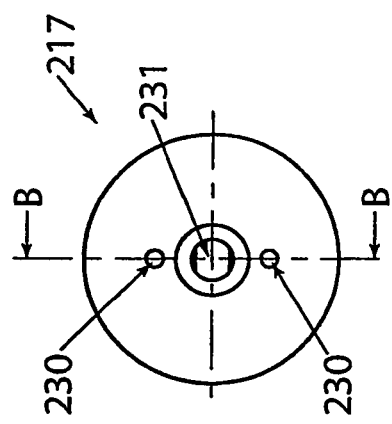
FIG. 11B is an end view of the male end shown in FIG. 11A.
Figure 11E:
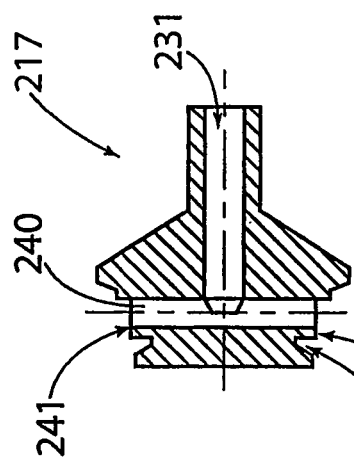
FIG. 11E is a side cross-sectional view of the male end shown in FIG. 11D, taken along the lines A-A.
Figure 11D:
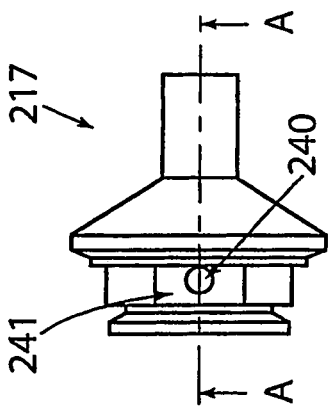
FIG. 11D is a side view of the male end shown in FIG. 11A.

FIG. 9 shows a cross-sectional representation of bellows 214 (in its relaxed state) of a roughly cylindrical form, for use in the pressure indication device 210. The bellows 214 may alternatively be employed in other embodiments of the pressure indication device, providing those embodiments have internal wall ribs 213 for guiding and stabilizing the movement of the bellows as it contracts or expands within the device. In this embodiment of the bellows, the closed end portion 254 is modified somewhat relative to the previously described embodiment. The closed end 254 does not have a boss formed on its end. The indication mark is not provided on a flange connected to the closed end, but is instead formed on an outer annular edge of the last pleat toward the closed end 254. The indication marks are shown in FIGS. 8 and 9 and designated by reference numeral 238. These indication marks may be formed as a paint or dye applied to the bellows 214 after it is molded. This paint or dye must contrast with the color of the material used for the bellows. For example, if the bellows is formed of a white or generally translucent material, the indicator mark 238 should be of a contrasting dark color. In this embodiment, as there is no disk and flange to guide movement of the bellows within the outer wall 212, this guiding and stabilizing function is performed by larger diameter pleats 260 (including the end pleat on which indicator marks 238 are formed), in cooperation with the internal wall ribs 213. In the embodiment of the bellows 214 shown in FIG. 9, the last and third-from-last pleats in the bellows are enlarged so as to contact the internal wall ribs 213 as they move longitudinally within the device 210. This stabilization is important so that the orientation of the indication mark relative to the scale markings on the outside of the outer wall 212 is not skewed during compression of the bellows 214, which may lead to an inaccurate pressure reading. Additionally, thickened portions 239 are provided between the last three pleats toward the closed end 254 to stiffen the end part of the bellows 214. This stiffening assists in stabilizing the travel of the bellows and thus the indication mark. The thickened portions 239 also serve to minimize movement of the last pleat on which the indication mark 238 is formed relative to other pleats during compression of the bellows 214, thus assisting in calibration of the device for serving its pressure indication function. These thickened portions 239 may be formed around the circumference of the bellows 214 in the relevant pleat position or may be formed as circumferentially spaced ribs connecting the pleats at a number of points for stiffening thereof.

As shown in FIG. 9, the outer diameter of smaller pleats 258, indicated by a, is less than the outer diameter of the larger diameter pleats 260, represented by b. The difference between b and a is preferably about 0.2 mm. For example, b may be 9.8 mm and a may be 9.6 mm.

The bellows 214 has a flange 256 at its open end 252 for fitting into and engaging with the rebate 227, as shown in FIG. 8.

The function of male end 217 is generally illustrated with respect to FIG. 8. Referring now to FIGS. 11A to 11E, it can be seen that the representation of male end 217 in FIG. 8 corresponds to that of FIG. 11C. What is not shown in FIG. 8, however, is how outlet fluid communication channel 240 communicates with outer chamber 232. This is more apparent from FIGS. 11A, 11D and 11E, in which it can be seen that the male end 217 has flattened side portions 241 where the outlet fluid communication channel 240 opens out to the sides of male end 217. These flattened side portions 241 allow a small gap between the outside of male end 217 and outer wall 212 for providing fluid communication between outlet fluid communication channel 240 (and thus outlet passage 231) and outer chamber 232.

Referring now to FIGS. 12A, 12B and 12C, it can be seen that the valve support plate 219 is generally disk shaped, but with a center hole 225 and additional holes formed toward a periphery of the disk shape so as to provide female end fluid channels 222. A raised portion of the disk acts as the stopper support flange 228 for supporting the outer annular base of the stopper 221, while the center hole 225 communicates with the concave interior of the stopper 221. The valve support plate 219 may be held in place within the outer wall 212 by use of adhesives or may be chemically, ultrasonically or laser welded in place. For additional support, valve support plate 219 may sit against the ends of internal wall ribs 213. This additional support may assist in resisting the force required to be applied to the stopper 221 to open the valve 220. The valve support plate 219 and male end 217 are preferably formed of Lexan or Ultem for the autoclavable embodiment or PVC for the non-autoclavable embodiment.

Figure 13:
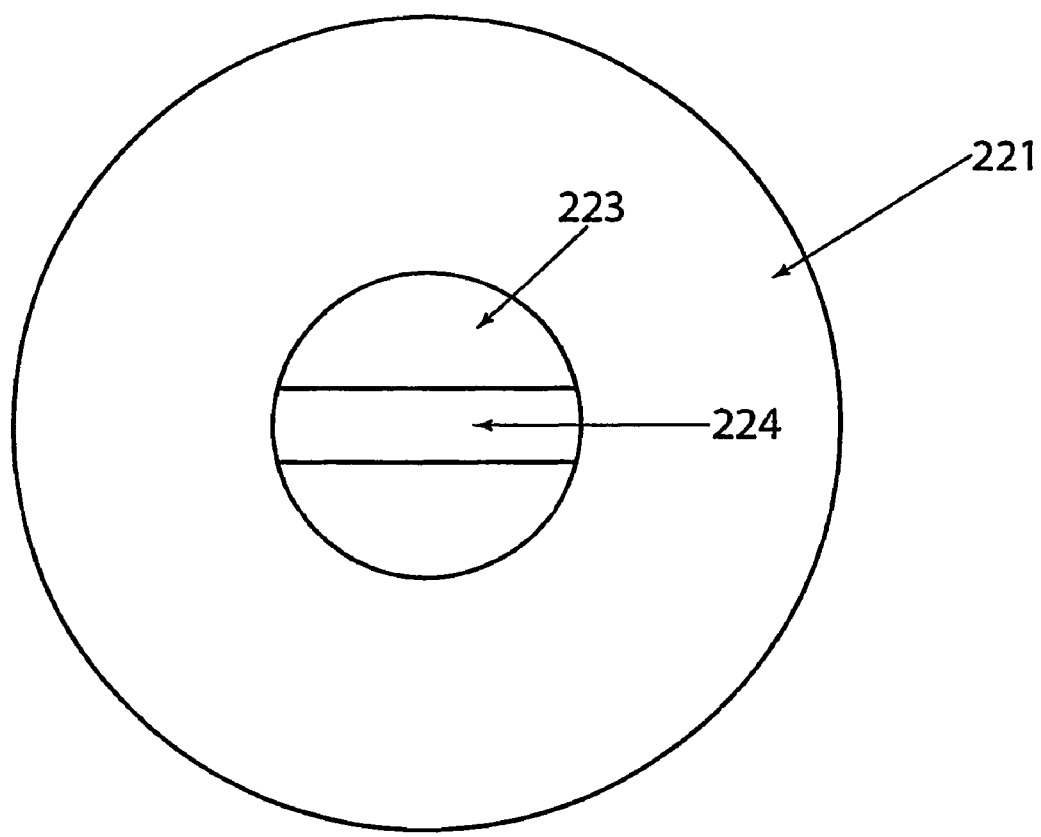
FIG. 13 is an end view of a stopper used in the pressure indication device shown in FIG. 8.

FIG. 13 is an end view of the stopper 221, as if looking toward it through the female end opening 226. The stopper head portion 223 and channel 224 are located centrally on an apex of the stopper 221. The depth of channel 224 need only be in the order of 0.5 mm or less, while the thickness of the head portion 223 may be in the order of 2 mm. The diameter of head portion 223 is formed so as to provide only a loose fit within female end opening 226 and is not intended to, in itself, occlude the opening.

While certain embodiments of the invention have been described above, it is specifically envisaged that different parts of the different embodiments may be used interchangeably to arrive at further embodiments. For example, the bellows 14, guiding arrangement and indicating mark arrangement shown and described in FIGS. 1, 2 and 5 may be substituted with that described in relation to FIGS. 8 and 9. Also, the male and female ends shown and described in relation to FIGS. 8, 11A to 11E, 12A to 12C, 13 and 14, may be used in place of male and female ends 17 and 16 described with reference to FIG. 1. Additionally, autoclavable and non autoclavable versions of each embodiment are envisaged, the difference residing in the choice of materials for each component. Further, a version of the embodiment shown and described in relation to FIG. 8 is envisaged for use in a manner similar to that shown and described in relation to FIG. 6, such that it is non removably connected to a cuff inflation tube 64 of a laryngeal mask 125, such as is shown in FIG. 7.

The invention claimed is:

1. A device that indicates internal pressure of an inflatable medical cuff including:
   a hollow housing having a first opening at a first end thereof to which a cuff inflation tube can be coupled and a second opening at a second end of the hollow housing to which a syringe can be coupled, the hollow housing including a generally cylindrical body which is made from transparent material and an integral end formation which includes the second opening;

a valve in the second opening having a valve element which can be unseated from sealing engagement with a valve seat on coupling of the syringe to the second opening for permitting inflating air from the syringe to pass into or from the hollow housing; and a bellows having an open end and a closed end, the open end of the bellows coupled to the hollow housing at said first end to form an inner chamber within the bellows and an outer chamber between the bellows and the hollow housing, and wherein the closed end of the bellows is disposed towards the second end of the hollow housing, the hollow housing including at least one vent which vents the inner chamber to atmosphere, and wherein the hollow housing includes at least one fluid communication passage from the first opening to the outer chamber and an end body which is coupled to the cylindrical body and includes the first opening, the at least one communication passage and the at least one vent and wherein the open end of the bellows is connected to the end body, whereby in use the outer chamber is at the same pressure as the internal pressure of the cuff, whereby changes in the internal pressure of the cuff cause expansion and retraction of the bellows such that the position of the closed end of the bellows indicates the internal pressure of the cuff.

2. The device according to claim 1, wherein the hollow housing is autoclavable and formed of one of polysulphone, Lexan and Ultem.

3. The device according to claim 1, wherein the hollow housing is generally cylindrical and has scale markings thereon with which a position of the closed end of the bellows may be compared to indicate the internal pressure of the cuff.

4. The device according to claim 1, wherein the valve element is unseated from the valve seat by engagement of an end of the syringe upon insertion of the syringe into the second opening to allow air communication from or into the syringe to or from the outer chamber.

5. The device according to claim 1, wherein the bellows is formed of silicone.

6. The device according to claim 5, wherein a wall thickness of the bellows is about 0.3 to 0.5 millimeters.

7. The device according to claim 6, wherein the wall thickness is about 0.4 millimeters.

8. The device according to claim 7, wherein pleats of the bellows have an opening angle of about sixty degrees when the bellows is in a relaxed state.

9. The device according to claim 8, wherein a flange is provided at the open end of the bellows for engaging a rebate in the hollow housing.

10. The device of claim 7, wherein the bellows has an outer diameter of between about 15 mm and 9 mm.

11. The device of claim 7, wherein at least one pleat of the bellows toward the closed end is less compressive than pleats toward the open end.

12. The device of claim 7, wherein at least one pleat toward the closed end is of a larger diameter than pleats toward the open end.

13. The device according to claim 1, wherein the outer chamber includes a substantially annular chamber between an inside wall of the hollow housing and the bellows and an end chamber between the second end of the hollow housing and the closed end of the bellows, the end chamber and the annular chamber being partially separated by a movable indicator.

14. The device according to claim 13, wherein the movable indicator is connected to the bellows at the closed end thereof.

15. The device of claim 13, wherein the movable indicator comprises an annular portion of the bellows disposed toward the closed end thereof.

16. The device of claim 15, wherein guide means are provided on the inside wall of the hollow housing for guiding movement of the bellows axially within the hollow housing.

17. The device of claim 16, wherein the guide means includes a plurality of longitudinally extending ribs.

18. The device of claim 17, wherein the ribs protrude from the inside wall by about 0.25 mm.

19. The device of claim 1, further comprising an indication mark formed on an outer annular portion of a pleat proximate to the closed end.

20. The device of claim 1, further comprising:
a laryngeal mask including the inflatable medical cuff having the cuff inflation tube coupled thereto.

* * * * *